(12) United States Patent
Zhang et al.

(10) Patent No.: US 10,666,901 B1
(45) Date of Patent: May 26, 2020

(54) SYSTEM FOR SOOTHING AN OCCUPANT IN A VEHICLE

(71) Applicant: DENSO International America, Inc., Southfield, MI (US)

(72) Inventors: Yu Zhang, Farmington Hills, MI (US); Bilal Alasry, Dearborn, MI (US); Te-Ping Kang, Ann Arbor, MI (US); Vikas Upmanue, Novi, MI (US); Jordan Necovski, Livonia, MI (US); Sean Bleicher, Fenton, MI (US); Doua Vang, Waterford, MI (US); Eleanor Duke, Sterling Heights, MI (US); Nicholaus Spunar, Canton, MI (US)

(73) Assignee: DENSO INTERNATIONAL AMERICA, INC., Southfield, MI (US)

( * ) Notice: Subject to any disclaimer, the term of this patent is extended or adjusted under 35 U.S.C. 154(b) by 0 days.

(21) Appl. No.: 16/238,654

(22) Filed: Jan. 3, 2019

(51) Int. Cl.
| | |
|---|---|
| *H04N 7/15* | (2006.01) |
| *G06K 9/00* | (2006.01) |
| *G06F 3/16* | (2006.01) |
| *H04N 5/33* | (2006.01) |
| *H04B 1/38* | (2015.01) |
| *H04L 29/08* | (2006.01) |

(52) U.S. Cl.
CPC ............... *H04N 7/15* (2013.01); *G06F 3/16* (2013.01); *G06K 9/00832* (2013.01); *H04N 5/33* (2013.01); *H04B 1/38* (2013.01); *H04L 67/306* (2013.01)

(58) Field of Classification Search
CPC ........ H04N 7/15; H04N 5/33; G06K 9/00832; G06F 3/16; H04B 1/38; H04L 67/306
See application file for complete search history.

(56) References Cited

U.S. PATENT DOCUMENTS

| | | | | |
|---|---|---|---|---|
| 5,544,649 | A | * | 8/1996 | David .................. A61B 5/6887 600/301 |
| 7,308,341 | B2 | | 12/2007 | Schofield et al. |
| 7,597,393 | B1 | | 10/2009 | Tuccinardi et al. |
| 8,516,514 | B2 | * | 8/2013 | Belz .................. G08B 21/0423 340/539.25 |
| 2001/0054071 | A1 | * | 12/2001 | Loeb .................. H04L 12/1822 709/205 |

(Continued)

FOREIGN PATENT DOCUMENTS

| | | | | |
|---|---|---|---|---|
| CN | 205901926 | * | 1/2017 | ............... H04N 7/14 |
| EP | 3537712 | * | 9/2019 | ............. H04N 7/147 |

*Primary Examiner* — Oyesola C Ojo
(74) *Attorney, Agent, or Firm* — Brooks Kushman P.C.

(57) ABSTRACT

A system in a vehicle comprises one or more sensors configured to obtain occupant information indicating a stress level of an occupant of the vehicle. The system also includes a wireless transceiver in communication with a mobile device including a camera configured to monitor the occupant, and a controller in communication with the one or more sensors and the wireless transceiver, wherein the controller is configured to determine a stress-level of the occupant utilizing at least the occupant information, initiate a video conference session on the mobile device between the occupant and one or more contacts of the occupant in response to the determination of the stress level of the occupant exceeding a threshold, and output on a vehicle display the video conference between the occupant and the one or more contacts.

20 Claims, 4 Drawing Sheets

(56) References Cited

U.S. PATENT DOCUMENTS

| | | | |
|---|---|---|---|
| 2009/0296909 A1* | 12/2009 | Anglin | H04M 3/56 |
| | | | 379/202.01 |
| 2014/0067801 A1* | 3/2014 | Marvit | G06F 16/29 |
| | | | 707/736 |
| 2014/0118548 A1 | 5/2014 | Veneziano et al. | |
| 2015/0371456 A1* | 12/2015 | Moore, Jr. | G07C 5/008 |
| | | | 701/1 |
| 2016/0104486 A1 | 4/2016 | Penilla et al. | |
| 2016/0205146 A1* | 7/2016 | Sugioka | H04L 65/1066 |
| | | | 709/204 |
| 2016/0302391 A1* | 10/2016 | Pantazes | A01K 29/005 |
| 2017/0334263 A1* | 11/2017 | Schumacher | B60N 2/56 |
| 2017/0347002 A1* | 11/2017 | Baker | H04N 5/232 |
| 2017/0353693 A1* | 12/2017 | Semsey | B60N 2/002 |
| 2019/0069778 A1* | 3/2019 | Pourhoseini | A61B 5/0022 |
| 2019/0168669 A1* | 6/2019 | Lintz | B60R 1/00 |

* cited by examiner

SYSTEM FOR SOOTHING AN OCCUPANT IN A VEHICLE

TECHNICAL FIELD

The present disclosure relates to video conferencing in a vehicle.

BACKGROUND

Mobile phones may allow for video conferencing between two or more people. The video conferencing feature of a mobile phone may be utilized both inside and outside of a vehicle. During certain scenarios in a vehicle, the video conferencing system may be utilized to allow a child to video conference an adult.

SUMMARY

According to one embodiment, a system in a vehicle comprises one or more sensors configured to obtain occupant information indicating a stress level of an occupant of the vehicle. The system also includes a wireless transceiver in communication with a mobile device including a camera configured to monitor the occupant, and a controller in communication with the one or more sensors and the wireless transceiver, wherein the controller is configured to determine a stress-level of the occupant utilizing at least the occupant information, initiate a video conference session on the mobile device between the occupant and one or more contacts of the occupant in response to the determination of the stress level of the occupant exceeding a threshold, and output on a vehicle display the video conference between the occupant and the one or more contacts.

According to a second embodiment, a system in a vehicle comprises one or more sensors configured to obtain occupant information indicating a stress level of an occupant of the vehicle, a camera located in the vehicle and configured to monitor the occupant, and a controller in communication with the one or more sensors, wherein the controller is configured to determine a stress load of the occupant utilizing at least information indicative of the stress load, initiate a video conference session between the occupant and one or more contacts associated with the occupant in response to the stress load exceeding a threshold, and output the video conference session on a vehicle display associated with the occupant.

According to one embodiment, a system in a vehicle comprises one or more sensors configured to obtain stress-load information indicative of a stress load of an occupant of the vehicle, a controller in communication with the one or more sensors, wherein the controller is configured to determine a stress load of the occupant utilizing at least the stress-load information, initiate a video conference session between the occupant and one or more contacts associated with the occupant in response to the stress load exceeding a threshold, wherein the video conference session is initiated utilizing an in-vehicle camera, and output the video conference session on a vehicle display associated with the occupant.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Figure 1:
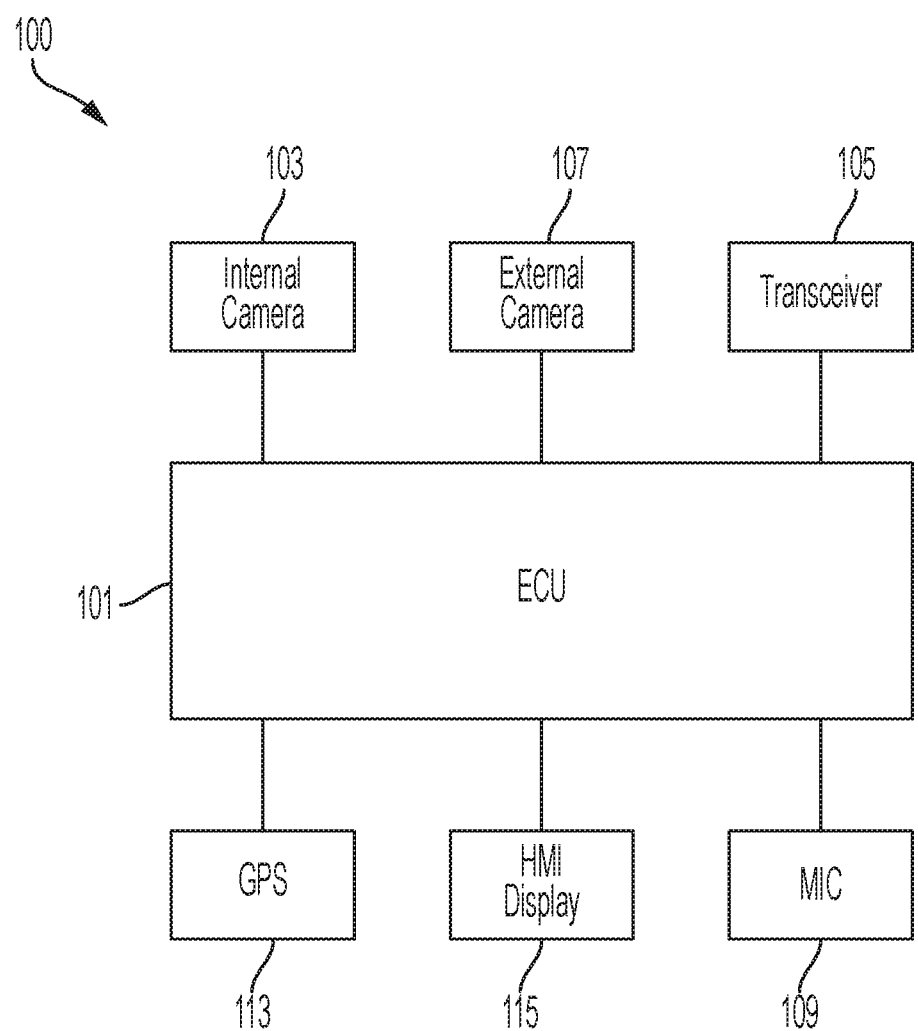
FIG. 1 illustrates an example block diagram of a vehicle system 100. The system 100 may include a controller 101.

FIG. 1 illustrates an example block diagram of a vehicle system 100. The system 100 may include a controller 101. The controller 101 may be a vehicle controller such as an electronic control unit (ECU). The controller 101, also referred to herein as ECU 101, may be embodied in a processor configured to carry out instructions for the methods and systems described herein. The controller 101 may include a memory (not individually shown in FIG. 1), as well as other components specific processing within the vehicle. The controller 101 may be one or more computing devices such as a quad core processor for processing commands, such as a computer processor, microprocessor, or any other device, series of devices or other mechanisms capable of performing the operations discussed herein. The memory may store instructions and commands. The instructions may be in the form of software, firmware, computer code, or some combination thereof. The memory may be in any form of one or more data storage devices, such as volatile memory, non-volatile memory, electronic memory, magnetic memory, optical memory, or any other form of data storage device. In one example, the memory may include 2 GB DDR3, as well as other removable memory components such as a 128 GB micro SD card.

The controller 101 may be in communication with various sensors, modules, and vehicle systems both within and remote of a vehicle. The system 100 may include such sensors, such as various cameras, a LIDAR sensor, a radar sensor, an ultrasonic sensor, or other sensor for detecting information about the surroundings of the vehicle, including, for example, other vehicles, lane lines, guard rails, objects in the roadway, buildings, pedestrians, etc. In the example shown in FIG. 1, the system 100 may include an in-vehicle camera 103, a transceiver 105, a sound identification device 109, a GPS module 113, a human-machine interface (HMI)

display as well as other sensors, controllers, and modules. FIG. 1 is an example system and the system 100 may include more or less sensors, and of varying types. Further, while the vehicle of FIG. 1 is shown with specific sensors in specific locations for purposes of illustration, the system 100 may be equipped with additional sensors at different locations within or on the vehicle, including additional sensors of the same or different type. As described below, such sensors may be utilized to determine a cognitive load of an occupant of the The vehicle system 100 may be equipped with a transceiver 105. The transceiver 105 may be a BLUETOOTH transceiver. In one illustrative embodiment, the system 100 uses the BLUETOOTH transceiver 105 to communicate with a user's mobile device (e.g., cell phone, smart phone, PDA, tablet, or any other device having wireless remote network connectivity). The mobile device can then be used to communicate with a network outside the vehicle system 100 through, for example, communication with a cellular tower. In some embodiments, tower may be a WiFi access point.

If the user has a data-plan associated with the mobile device, it is possible that the data-plan allows for broad-band transmission and the system could use a much wider bandwidth (speeding up data transfer). In still another embodiment, mobile device is replaced with a cellular communication device (not shown) that is installed to vehicle. In yet another embodiment, the mobile device may be a wireless local area network (LAN) device capable of communication over, for example (and without limitation), an 802.11g network (i.e., WiFi) or a WiMax network. In one embodiment, incoming data can be passed through the mobile device via a data-over-voice or data-plan, through the onboard BLUETOOTH transceiver and into the vehicle's ECU 101. In the case of certain temporary data, for example, the data can be stored on the HDD or other storage media until such time as the data is no longer needed.

In another embodiment, the transceiver 105 may be on on-board communication device or cellular modem. The on-board communication device may not require a cellular phone (e.g. mobile device) to be paired with a BLUETOOTH transceiver to communicate to an off-board server. Instead, the on-board modem may have its own capability to communicate with an off-board network.

An in-vehicle camera 103 may be mounted in the vehicle to monitor occupants (e.g. a driver or passenger) within the vehicle cabin. The in-vehicle camera 103 may be part of an occupant status monitoring system (OSM). The in-vehicle camera 103 may be utilized to capture images of an occupant in the vehicle. The in-vehicle camera 103 may obtain facial information about an occupant, such as eye-movement of the occupant and head-movement of the occupant, as discussed further below. The in-vehicle camera may be a color camera, infrared camera, or time of flight camera. The in-vehicle camera 103 may be mounted on a head rest, in the headliner, or located on a mobile device (e.g. tablet or mobile phone) to capture the driver's face, especially the driver's eyes.

A controller may receive driver status data from the OSM to determine an abnormal situation within the vehicle. The OSM employs one or more activity sensors such as a driver-facing camera, an occupant-facing camera, a health scanner, and an instrument panel to monitor activities performed by the driver or occupants (e.g. passengers in the vehicle). Based on the activity sensors, the OSM may determine whether the driver is, for example, distracted, sick, or drowsy as the abnormal situation.

A controller may receive occupant status data from the OSM to determine an abnormal situation within the vehicle. The OSM may employ one or more activity sensors such as a occupant-facing camera, a health scanner, and an instrument panel to monitor activities performed by occupants. For example, an occupant-facing camera may be employed in a vehicle headliner, vehicle headrest, or other area of the vehicle to monitor activity of the occupant. The OSM may also employ a mic that is in communication with a voice recognition (VR) engine that can detect fussiness of a child (e.g. baby) or irregular crying or sounds from the child. Based on the activity sensors, the OSM may determine whether the occupant or driver is, for example, fuss, experiencing motion sickness, hunger and fever.

A health scanner may be mounted on the vehicle seat, child seat, or suitable location which the occupant touches. The health scanner may scan the occupant's heartbeat. The OSM processes data received from the health scanner and monitors whether the occupant is suffering from a severe physical condition or episode. The OSM may also be utilized with the health scanner to see if various fluctuations in data may identify stress or issues with the occupant.

The vehicle system 100 may include at least one external camera 107. The external camera 107 may be mounted in the rear-view mirror. The external camera 107 may also be facing out of the vehicle cabin through a vehicle's windshield to collect imagery data of the environment in front of the vehicle. The external camera 107 may be utilized to collect information and data regarding the front of the vehicle and for monitoring the conditions ahead of the vehicle. The camera 107 may also be used for imaging the conditions ahead of the vehicle and correctly detecting the positions of lane markers as viewed from the position of the camera and the presence/absence, for example, of lighting of the head lights of oncoming vehicles. For example, the external camera 107 may be utilized to generate image data related to vehicle's surrounding the vehicle, lane markings ahead, and other object detection. A vehicle may also be equipped with a rear camera (not shown) for similar circumstances, such as monitoring the vehicle's environment around the rear proximity of the vehicle.

The system may be equipped with a vehicle mic 109 or sound identification device 109. The sound identification device 109 determines a probability that the sound data corresponds to a pre-defined sound based on the subset of temporal parameters. In the illustrative embodiment, the sound identification device 109 applies an algorithm (e.g. trained deep-neural-network) to determine if an occupant event is occurring. In the illustrative embodiment, the algorithm takes a number of inputs corresponding to the number of temporal parameters. Each acoustic feature vector may include a number of features and temporal parameters that are determined for each acoustic feature. Of course, in other embodiments, the number of parameters may vary. The deep-neural-network algorithm of the illustrative sound identification device 109 may have previously been trained using machine learning in order to accurately determine if the sound data matches a pre-defined sound. The deep-neural-network algorithm may employ a softmax layer, backpropagation, and cross-entropy optimization as part of the training. This training may include supplying samples of sounds that match the pre-defined sound and samples of sounds that do not match the pre-defined sound, such as sounds similar to expected background noise. For example, if the pre-defined sound is an infant crying, the algorithm may be provided with a number of samples of infants crying as well as sounds similar to expected background noise such as adult conversation, road traffic noise, and other vehicle sounds. In some embodiments, the sound identification device 109 may determine whether the sound corresponds to several different pre-defined sounds, such as a baby crying, a baby babbling, a cough, or background sounds.

The system 100 may also include a global positioning system (GPS) 113 that detects or determines a current position of the vehicle. In some circumstances, the GPS 113 may be utilized to determine a speed that the vehicle is traveling. The system 100 may also include a vehicle speed sensor (not shown) that detects or determines a current speed that the vehicle is traveling. The system 100 may also include a compass or three-dimensional (3D) gyroscope that detects or determines a current direction of the vehicle. Map data may be stored in the memory. The GPS 113 may update the map data. The map data may include information that may be utilized with advanced driver assistance system (ADAS). Such ADAS map data information may include detailed lane information, slope information, road curvature data, lane marking-characteristics, etc. Such ADAS map information may be utilized in addition to traditional map data such as road names, road classification, speed limit information, etc. The controller 101 may utilize data from the GPS 113, as well data/information from the gyroscope, vehicle speed sensor, and map data, to determine a location or current position of the vehicle.

The system 100 may also include a human-machine interface (HMI) display 115. The HMI display 115 may include any type of display within a vehicle cabin. Such HMI displays may include a dashboard display, navigation display, multimedia display, heads-up display, thin-film transistor liquid-crystal display (TFT LCD), etc. The HMI display 115 may also be connected to speakers to output sound related to commands or the user interface of the vehicle. The HMI display 115 may be utilized to output various commands or information to occupants (e.g. driver or passengers) within the vehicle. For example, in a rear-seat occupant stress out scenario, the HMI display 115 may display message to the driver that the rear-seat occupant is stressed and need comfort. The HMI display 115 may utilize any type of monitor or display utilized to display relevant information to the occupants. The HMI display 115 may also include a heads-up display ("HUD") that is utilized to display an interface and other objects on a windshield so that the images are within a driver's periphery while driving or in an occupant's line of sight.

In addition to providing visual indications, the HMI display 115 may also be configured to receive user input via a touch-screen, user interface buttons, etc. The HMI display 115 may be configured to receive user commands indicative of various vehicle controls such as audio-visual controls, autonomous vehicle system controls, certain vehicle features, cabin temperature control, etc. The controller 101 may receive such user input and in turn command a relevant vehicle system of component to perform in accordance with the user input.

The HMI display 115 may also include a display that is embedded into a headrest of a vehicle. The HMI display 115 that is embedded into the headrest may also include a built-in camera that can face the occupant. The HMI display 115 may be facing an occupant of a vehicle (e.g. baby) to allow the occupant to interact with the HMI display or to monitor issues.

The controller 101 can receive information and data from the various vehicle components including the in-vehicle camera 103, external camera 105, the GPS 113 and the HMI display 115. The controller 101 utilize such data to provide vehicle functions that may relate to driver assistance, or autonomous driving. For example, data collected by the in-vehicle camera 103, sound identification device 109, and the forward camera 107 may be utilized in context with the GPS data and map data to provide or enhance functionality related to adaptive cruise control, automatic parking, parking assist, automatic emergency braking (AEB), etc. The controller 101 may be in communication with various systems of the vehicle (e.g. the engine, transmission, brakes, steering mechanism, display, sensors, user interface device, etc.). For example, the controller 101 can be configured to send signals to the brakes to slow the vehicle 100, or the steering mechanism to alter the path of vehicle, or the engine or transmission to accelerate or decelerate the vehicle. The controller 101 can be configured to receive input signals from the various vehicle sensors to send output signals to the display device, for example. The controller 101 may also be in communication with one or more databases, memory, the internet, or networks for accessing additional information (e.g. maps, road information, weather, vehicle information). The controller may also be utilized with the internal camera 103 to identify facial features of an occupant of the vehicle, as explained in more detail below.

Figure 2:
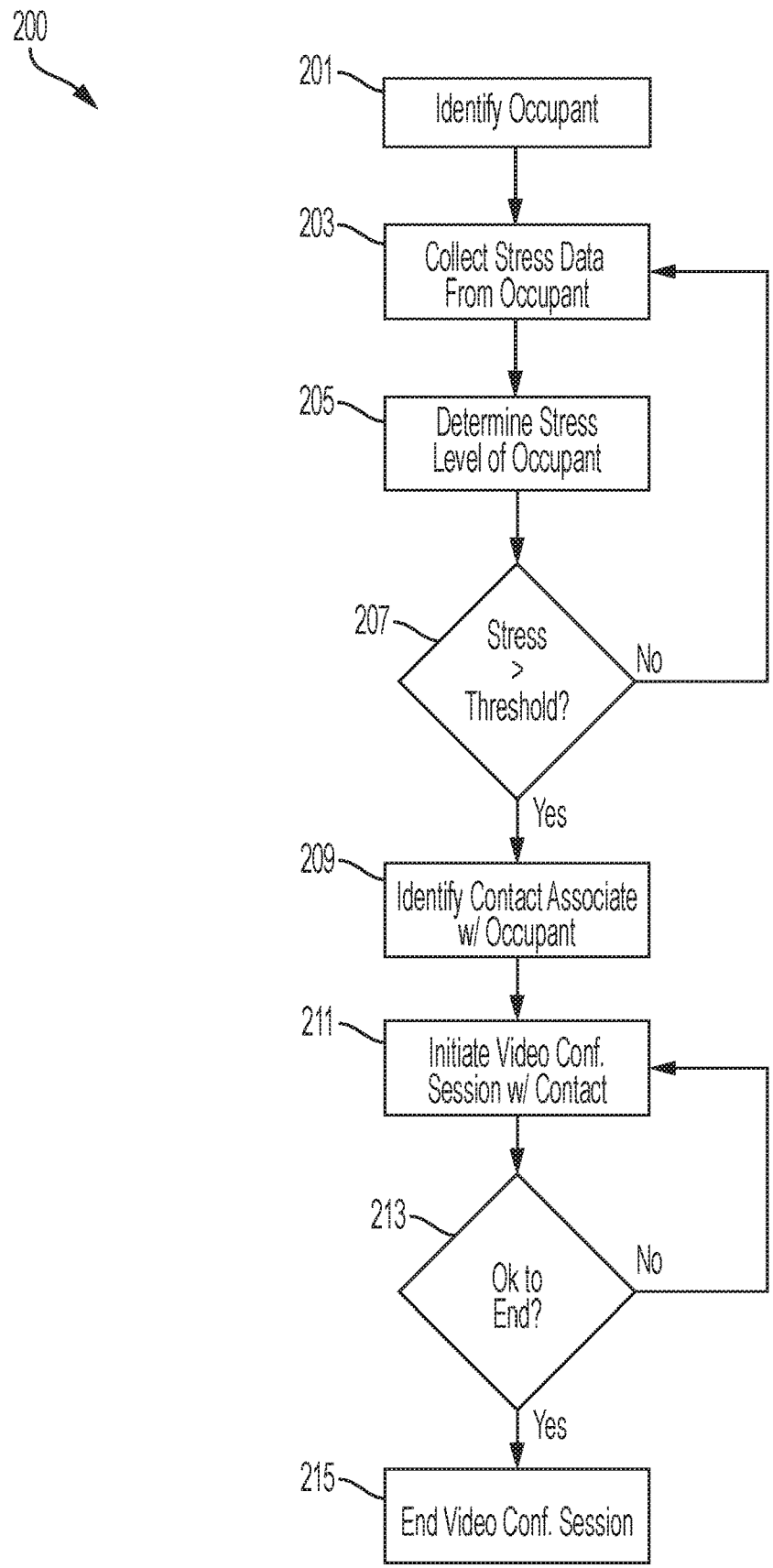
FIG. 2 is an exemplary flow chart 200 of a vehicle system for initiating a video conferencing in response to a stress load of an occupant.

FIG. 2 is an exemplary flow chart 200 of a vehicle system for initiating a video conferencing in response to a stress load of an occupant. For example, a video conference call to a grandparent may be initiated if the system detects a fussy or cranky baby. The flow chart 200 may be implemented on a vehicle side application in a vehicle controller or off-board at a remote server. The system may first attempt to identify if an occupant is present or who the occupant is at step 201. The system may utilize an internal camera and utilize facial recognition to identify the occupant. Certain vehicle settings may also be attributed with an occupant of the vehicle. For example, a certain child seat may have a certain vehicle seat configuration that needs to be adjusted for that seat. Additionally, a weight sensor in a seat may be utilized to identify if an occupant is present.

The system may also be configured to collect stress data from an occupant at step 203. The system may utilize various sensors in the vehicle to help determine a stress load of the vehicle. For example, the system may utilize a camera to track movement and facial expressions (e.g. utilizing facial recognition data) to collect information about the occupant. In another example, a vehicle mic may be in communication with a voice recognition engine that is configured to detect crying or fussiness of an occupant. The voice recognition engine may be able to match certain sounds from the occupant with crying. In another embodiment, the voice recognition engine may be able to collect fluctuations in tone or speech and attribute that to fussiness of an occupant (e.g. child or baby).

One or more sensors in the vehicle may obtain data that is utilized to identify a cognitive load of an occupant of the car, e.g. cognitive-load data. For example, the cognitive load data may be data acquired from information obtained from various vehicle sensors (e.g. camera, radar, LiDar, in-vehicle camera, speed sensor, windshield wiper sensor, biometric sensor, etc.) as well as off-board servers. The vehicle may utilize other sensors, such as fog lights, windshield wipers, rain sensor may also be utilized as inputs to determining the cognitive load. When a fog light is activated, or the windshield wipers are moving faster, or a rain sensor identifies higher precipitation, the driver's cognitive load may be high.

At another level, the cognitive load of the driver may be determined by an in-vehicle camera (e.g. camera 103) that monitors facial movement, eye-movement, etc. The cognitive load of the driver may be determined by an external camera (e.g. external camera 105) that monitors the surrounding vehicle environment. The camera may be utilized to identify surround vehicles, objects, pedestrians, etc. For example, if many vehicle or objects are surrounding the vehicle, the cognitive load of the driver may be higher. If the external camera fails to identify objects or just a limited amount of objects, the cognitive load of the driver may be low.

Furthermore, information may be utilized to identify a driver of the vehicle to adjust a threshold for a stress load of the driver. For example, an age of the occupant may factor into an occupant's stress load threshold being higher or lower. Identification of the occupant may be determined by user profile data or information obtained from a mobile phone, camera (e.g. facial recognition), or vehicle settings. For example, vehicle settings associated with the occupant may include climate controls associate with a climate zone of the occupant. The system may determine from historical data that certain occupants have certain climate settings, and thus associate the occupant with a user profile based on those settings. In another embodiment, system may determine from historical data that certain occupants have certain seating settings, and thus associate the occupant with a user profile based on those settings.

At step 205, the system may determine the stress load of the occupant utilizing the data collected by the various sensors in the vehicle. The system may adjust the threshold based on various factors in the vehicle, such as an occupant of the car. The system may also allow for automatic adjustment of the threshold that may be set by the user or adjusted via a vehicle interface. As such, the stress load data may be collected and analyzed to measure and compare against the threshold to determine how the vehicle system can initiate a video conference session based on a stress load of an occupant of a user.

At step 207, the system may compare the stress level of the occupant to that of the defined threshold. As previously discussed, the threshold may be adjusted based on the occupant or by an occupant in the vehicle via an in-vehicle HMI. If the stress load is determined to be below a threshold to initiate some countermeasure for the stress, the system may simply continue to collect stress data and monitor the occupant. However, if the stress exceeds the threshold, the system may identify an action to take that may reduce the stress of the occupant. In one example discussed below, the system may initiate a conference call between the occupant and a contact associated with the occupant.

At step 209, the vehicle system may identify one or more contacts associated with the occupant. A contact database may be in communication with the system that stores one or more contacts associated with the occupant. The contact database may be utilized and in communication with a mobile phone associated of a driver or other occupant in the vehicle to make a call to the contact. The contact in some instances may be related to the occupant or a care-giver (e.g. nanny or babysitter) to the occupant. The contact may be someone other than the driver or may be a driver as well. The contact database may be on a mobile phone associated with a driver or occupant. In another scenario, the vehicle system may have a contact list associated with certain occupants in the vehicle. Furthermore, a voice recognition system or user interface may allow an occupant or driver of the vehicle to select or input which contact to begin initiation of a video conference session.

At step 211, the vehicle system may initiate a video conference session with the one or more contacts. The video conference session may be initiated with a mobile device in the vehicle or via an embedded vehicle system with the ability to make or initiate video conference sessions. The embedded system may include a camera facing the occupant, an HMI display, a wireless transceiver to communicate with the cloud or data communication network, speakers, a mic, etc. The system may initiate the session with the mobile device or embedded system depending on various system features. For example, in one embodiment the system may initiate a conference call to a grandparent of a fussy child utilizing an iPad attached to a headrest that is communication with the vehicle via a Bluetooth transceiver.

At step 213, the vehicle system may analyze when to end the video conference session with the one or more contacts. The system may be configured to analyze the stress level of the occupant during a video conference session. The system may see if the stress level has subsided and reduced below a threshold level. At that point, it may end the conference session automatically. The system may utilize other factors to determine when to end the video conference session. For example, if the video conference session has not reduced a stress level for a threshold time (e.g. 5 minutes, 10 minutes, 20 minutes, etc.) or has in fact increased a stress level of the occupant, then the system may terminate the session given that the video conference session was not soothing the occupant. The interface may provide the stress level of the occupant to the other contact who is on the call. The contact may decide to end the call based on those information.

At step 215, the system may end the video conference session if the analyzing the stress level of the occupant shows that the stress level of the occupant has dropped below a defined threshold. The system may then terminate the video conference session and begin to analyze the stress count. Furthermore, the system may be programmed to send an alert or message (e.g. text or audible) to the contact person to let them know that the video conference session is ending or will be ending (e.g. with a countdown).

Figure 3:
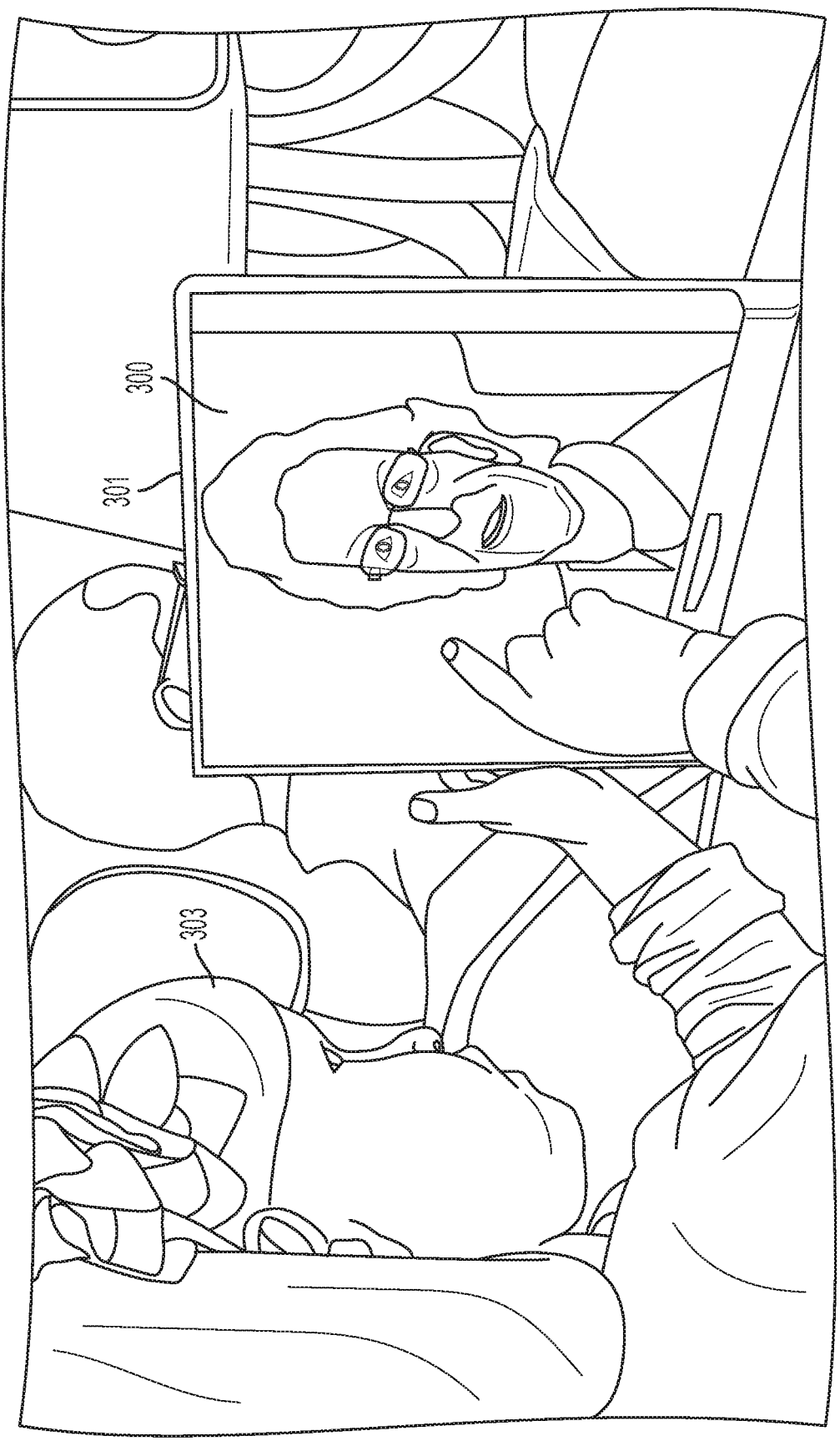
FIG. 3 is an example scenario of a video conference session being initiated in response to feedback from an occupant in the vehicle.

FIG. 3 is an example scenario of a video conference session being initiated in response to feedback from an occupant in the vehicle. As shown in FIG. 3, the screen 300 may display information regarding the video conference session. The screen 300 may be a screen (e.g. a touch screen) that is located on an integrated monitor, a mobile device 301 (e.g. phone, tablet, portable monitor etc.). The screen 300 may show information regarding the caller or caller ID information and video imagining from one or more contacts that are part of the contact database. The screen may show caller identification information, a call duration, an option to mute, option to use a keyboard, volume controls, add participants, add contacts, or mute the video conference session. The screen 300 may display video regarding a first user that is part of the video conference session. In another example, the video may also include an image of the occupant in the vehicle. In screen 300, the mobile device 301 may display video regarding a second user that is part of the video conference session.

Figure 4:
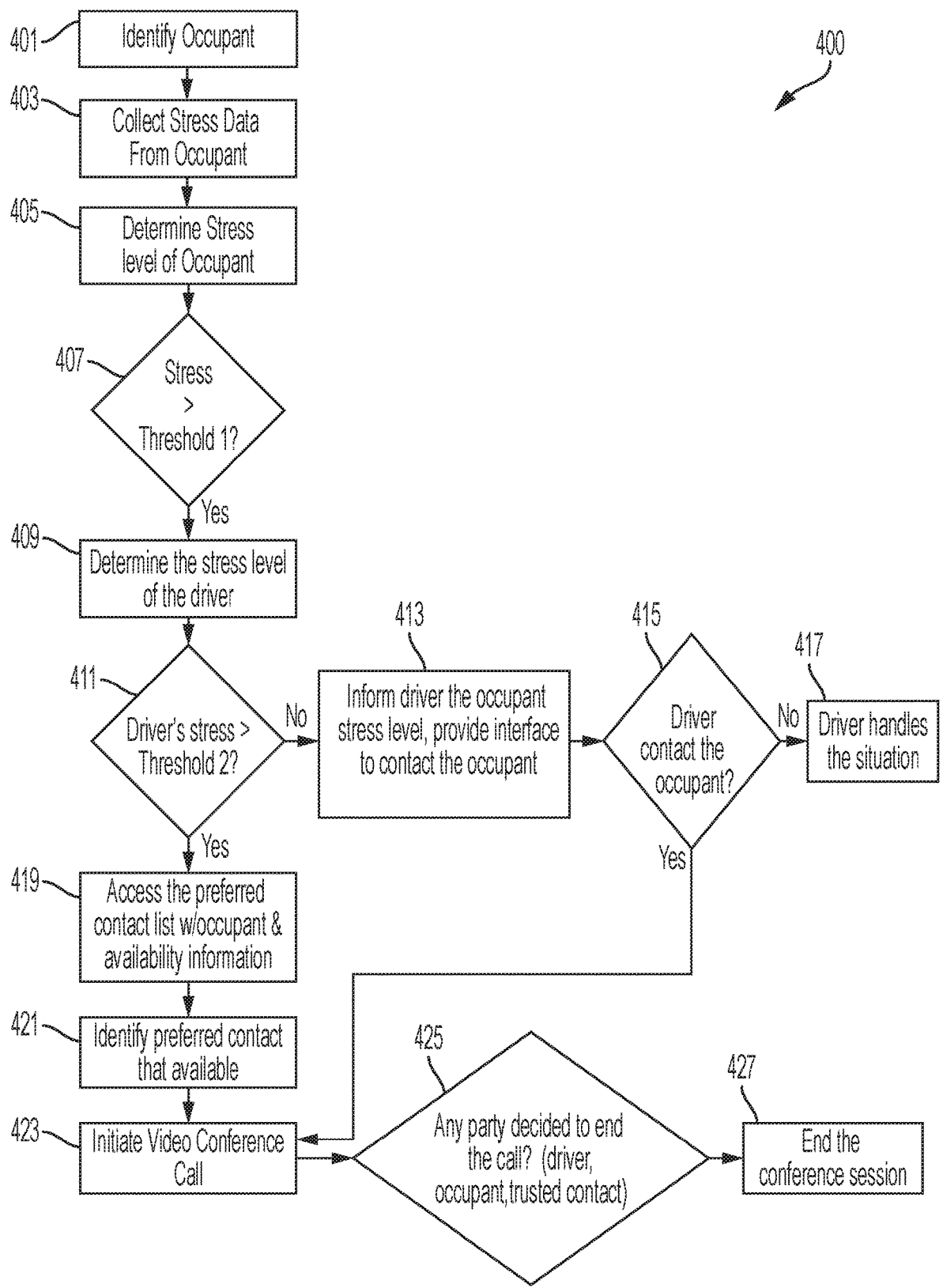
FIG. 4 is an exemplary flow chart 500 of a vehicle system for initiating a video conferencing session in response to a stress load of an occupant and a driver in an alternate embodiment.

FIG. 4 is an exemplary flow chart 500 of a vehicle system for initiating a video conferencing session in response to a stress load of an occupant and a driver in an alternate embodiment. The system may first attempt to identify if an occupant is present or who the occupant is at step 401. The system may utilize an internal camera and utilize facial recognition to identify the occupant. Certain vehicle settings may also be attributed with an occupant of the vehicle. For example, a certain child seat may have a certain vehicle seat configuration that needs to be adjusted for that seat. Additionally, a weight sensor in a seat may be utilized to identify if an occupant is present.

The system may also be configured to collect stress data from an occupant at step 403. The system may utilize various sensors in the vehicle to help determine a stress load of the vehicle. For example, the system may utilize a camera to track movement and facial expressions (e.g. utilizing facial recognition data) to collect information about the occupant. In another example, a vehicle mic may be in communication with a voice recognition engine that is configured to detect crying or fussiness of an occupant. The voice recognition engine may be able to match certain sounds from the occupant with crying. In another embodiment, the voice recognition engine may be able to collect fluctuations in tone or speech and attribute that to fussiness of an occupant (e.g. child or baby).

At step 405, the system may determine the stress load of the occupant utilizing the data collected by the various sensors in the vehicle. The system may adjust the threshold based on various factors in the vehicle, such as an occupant of the car. The system may also allow for automatic adjustment of the threshold that may be set by the user or adjusted via a vehicle interface. As such, the stress load data may be collected and analyzed to measure and compare against the threshold to determine whether an intervention should be applied to occupant based on a stress load of an occupant of a user.

At step 407, the system may compare the stress level of the occupant to that of the defined first level threshold of the occupant. As previously discussed, the threshold may be adjusted based on the occupant or by an occupant in the vehicle via an in-vehicle HMI. If the stress load is determined to be below a threshold to initiate some countermeasure for the stress, the system may simply continue to collect stress data and monitor the occupant. However, if the stress exceeds the threshold, the system may identify an action to take that may reduce the stress of the occupant. In one example discussed below, the system may issue a warning to the driver that the occupant need attention.

Ate step 409, the system may determine a stress level of the driver. The sensors may utilize similar sensors to those that are utilized for the occupant to identify a stress of the driver. For example, the system may utilize a camera to track movement and facial expressions (e.g. utilizing facial recognition data) to collect information about the driver. In another example, a vehicle mic may be in communication with a voice recognition engine that is configured to detect fluctuation of the voice of the driver or different tones of voice of the driver. The tone of the voice may be able to identify if the driver is upset, nervous, sad, etc. The voice recognition engine may be able to match certain sounds from the driver to those with a predefined sound that defines various tones of voice for the driver. In another embodiment, the system may "score" or "track" business of the vehicle environment for the driver based on the speed of the vehicle (e.g. utilizing a speed signal sensor), surrounding traffic of the vehicle (e.g. traffic data or camera/Radar sensors identifying vehicles/objects, buttons/business of user-interface HMI screen).

The system may then compare the stress level of the driver to that of a defined threshold level for the driver at step 411. The threshold may be adjusted based on the driver or by manually adjusted by an occupant in the vehicle via an in-vehicle HMI. If the stress load of the driver is determined to be below a threshold, the system may provide the driver an option to initiate a video conference session between the driver and the occupant. However, if the stress exceeds the threshold, the system may identify a contact other than driver to call so that action may be taken place to reduce the stress of the occupant without burden the driver. In one example discussed below, the system may initiate a conference call between the occupant and a contact associated with the occupant.

If the stress of the driver is below the threshold, the system may inform the driver the stress level of the occupant and provide an interface (e.g. HMI) that will allow the driver to initiate a video conference session with the occupant at step 413. The interface may be a voice recognition interface or a user-interface on the screen. The system may include an interface for initiating contact with the occupant based on the stress level of the occupant. For example, a driver may press a touch-screen button, steering wheel control/switch, or speak a voice recognition command to initiate the conference call with the occupant.

At decision 415, the system may decide whether or not the driver selected to contact or initiate a video conference session with occupant. If the driver does not select to contact the occupant via a video conference session or a phone call, the system may time out at 417 to let the driver handle the situation on their own. However, if the driver selects to contact the occupant, the system may initiate a video conference call at step 423. The video conference session may be initiated with a mobile device in the vehicle or via an embedded vehicle system with the ability to make or initiate video conference sessions. The embedded system may include cameras facing the driver and occupant, an HMI display, a wireless transceiver to communicate with the cloud or data communication network, speakers, a mic, etc. The system may initiate the session with the mobile device or embedded system depending on various system features. For example, in one embodiment the system may initiate a conference call to a grandparent of a fussy child utilizing an iPad attached to a headrest that is communication with the vehicle via a Bluetooth transceiver.

At decision 411, the system may determine that a driver's stress is greater than that of the threshold. In such a situation, the system may want to reduce the occupant stress level without the driver's involvement. The system may provide a preferred contact list with occupant and availability of the contact information at step 419. The interface may be a voice recognition interface or a user-interface on the screen. The contacts may be selected from a phonebook of the drive that is accessed via the Bluetooth protocol (e.g. Phonebook Access Profile or "PBAP".) In another embodiment, the system may include an interface for setting certain contacts based on the stressed occupant. The interface may allow different contacts for different occupants. For example, a first child occupant may have a first contact list and a second child occupant may have a second contact list. The driver may select a contact utilizing the interface at step 421. In one situation, the system at step 423 will initiate a video conference session with a contact that is available and capable of attempting to sooth an occupant. The system may have access to a calendar or schedule of contacts to determine availability of contacting one of the preferred contacts to soothe the occupant. In one scenario, the system may retrieve scheduling information from a preferred contact and see that the schedule indicates the contact is at work or at a meeting. Utilizing the scheduling information, the system may prevent initiation of the contact and look for a contact that is available based on the scheduling information.

At step 425, the vehicle system may determine if any of the parties have decided to end the call or video conference session. For example, the driver, occupant, or trusted occupant may have decided to end the call or video conference session. At step 427, the system may end the video conference session if a party has ended the session. The system may then terminate the video conference session and begin to analyze the stress count of the driver and occupants. Furthermore, the system may be programmed to send an alert or message (e.g. text or audible) to the contact person to let them know that the video conference session is ending or will be ending (e.g. with a countdown).

The system may also include an embodiment that may analyze when to end the video conference session with the one or more contacts based on a stress level of the occupant. The system may be configured to analyze the stress level of the occupant during a video conference session. The system may see if the stress level has subsided and reduced below a threshold level. At that point, it may end the conference session automatically. The system may utilize other factors to determine when to end the video conference session. For example, if the video conference session has not reduced a stress level for a threshold time (e.g. 5 minutes, 10 minutes, 20 minutes, etc.) or has in fact increased a stress level of the occupant, then the system may terminate the session given that the video conference session was not soothing the occupant.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A system in a vehicle, comprising:
   one or more sensors configured to obtain occupant information indicating a stress level of an occupant of the vehicle including a mic configured to obtain voice information from the occupant;
   a wireless transceiver in communication with a mobile device including a camera configured to monitor the occupant;
   a controller in communication with the one or more sensors and the wireless transceiver, wherein the controller is configured to:
   determine a stress level of the occupant utilizing at least the occupant information including fluctuations in tone or speech of the voice information from the occupant;
   initiate a video conference session on the mobile device with a remote mobile device of one or more contacts of the occupant in response to the determination of the stress level of the occupant exceeding a threshold and confirmation of a driver to initiate the video conference session; and
   output on a display the video conference between the occupant and the one or more contacts.

2. The system of claim 1, wherein the controller is further configured to obtain user profile information from a mobile phone of the driver via the wireless transceiver and initiate the video conference session with one or more contacts other than the driver.

3. The system of claim 1, wherein the mobile device includes the one or more sensors and the display.

4. The system of claim 1, wherein the controller is further configured to obtain user profile information from a key fob associated with the driver of the vehicle and not initiate the video conference session between the occupant and the driver.

5. The system of claim 1, wherein the controller is further configured to initiate termination of the video conference session in response to the determination of the stress level of the occupant falling below the threshold.

6. The system of claim 1, wherein the system further includes a camera configured to capture images of the occupant of a vehicle; and
   utilize the images of the occupant in the video conference session.

7. The system of claim 1, wherein the controller is configured to select the one or more contacts to initiate the video conference session with in response to at least identification of the driver of the vehicle.

8. The system of claim 1, wherein the one or more sensors includes a thermal camera configured to obtain thermal readings from the occupant.

9. The system of claim 1, wherein the video conference session includes a video image of two or more contacts.

10. A system in a vehicle, comprising:
    one or more sensors configured to obtain occupant information indicating a stress level of an occupant of the vehicle, wherein the one or more sensors includes at least a mic configured to obtain voice information from the occupant;
    a camera located in the vehicle and configured to monitor the occupant; and
    a controller in communication with the one or more sensors, wherein the controller is configured to:
    determine a stress load of the occupant utilizing at least information indicative of the stress load from at least the voice information of the occupant;
    initiate a video conference session between the occupant and one or more contacts associated with the occupant in response to the stress load exceeding a threshold and confirmation from a driver to initiate the video conference session; and
    output the video conference session on a display associated with the occupant.

11. The system of claim 10, wherein the controller is further configured to obtain user profile information from vehicle settings associated with the occupant of the vehicle and adjust the threshold in response to the user profile information.

12. The system of claim 11, wherein the vehicle settings associated with the occupant include climate controls associate with a climate zone of the occupant.

13. The system of claim 11, wherein the vehicle settings associated with the occupant include seating controls associated with a vehicle seat of the occupant.

14. The system of claim 10, wherein the controller is configured select the one or more contacts to initiate the video conference session with in response to at least identification of the driver of the vehicle.

15. A system in a vehicle, comprising:
one or more sensors configured to obtain stress-load information indicative of a stress load of an occupant of the vehicle, wherein the one or more sensors includes at least a mic configured to obtain voice information from the occupant;
a controller in communication with the one or more sensors, wherein the controller is configured to:
determine the stress load of the occupant utilizing at least the voice information including fluctuations in tone or speech of the voice information from the occupant;
initiate a video conference session between the occupant and a remote mobile device of one or more contacts associated with the occupant in response to the stress load exceeding a threshold, wherein the video conference session is initiated utilizing an in-vehicle camera; and
output the video conference session on a mobile device associated with the occupant.

16. The system of claim 15, wherein the controller is further configured to select one or more contacts associated with the occupant to initiate the video conference session in response to at least identification of the occupant utilizing the in-vehicle camera.

17. The system of claim 15, wherein the controller is configured select the one or more contacts to initiate the video conference session in response to at least identification of a driver of the vehicle.

18. The system of claim 15, wherein the controller is further configured to initiate termination of the video conference session in response to a duration of the video conference session exceeding a time threshold.

19. The system of claim 15, wherein the controller is further configured to initiate termination of the video conference session in response to the determination of the stress load of the occupant falling below the threshold.

20. The system of claim 15, wherein the controller is configured select the one or more contacts to initiate the video conference session in response to a voice input from a driver of the vehicle.

* * * * *